(12) United States Patent
Samsonov et al.

(10) Patent No.: US 9,770,223 B2
(45) Date of Patent: Sep. 26, 2017

(54) SYSTEM AND METHOD FOR ACCELERATED, TIME-RESOLVED IMAGING

(71) Applicant: Wisconsin Alumni Research Foundation, Madison, WI (US)

(72) Inventors: Alexey A. Samsonov, Madison, WI (US); Julia V. Velikina, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 335 days.

(21) Appl. No.: 14/481,790

(22) Filed: Sep. 9, 2014

(65) Prior Publication Data

US 2016/0071291 A1    Mar. 10, 2016

(51) Int. Cl.
| | | |
|---|---|---|
| *A61B 5/05* | (2006.01) | |
| *A61B 6/00* | (2006.01) | |
| *A61B 5/055* | (2006.01) | |
| *A61B 6/03* | (2006.01) | |
| *G01R 33/561* | (2006.01) | |
| G01R 33/56 | (2006.01) | |
| G01R 33/563 | (2006.01) | |
| G01R 33/565 | (2006.01) | |

(52) U.S. Cl.
CPC ............... *A61B 6/504* (2013.01); *A61B 5/055* (2013.01); *A61B 6/032* (2013.01); *G01R 33/5611* (2013.01); *G01R 33/5601* (2013.01); *G01R 33/5635* (2013.01); *G01R 33/56308* (2013.01); *G01R 33/56366* (2013.01); *G01R 33/56509* (2013.01)

(58) Field of Classification Search
CPC ......... A61B 6/504; A61B 5/055; A61B 6/032; G01R 33/5611; G01R 33/5601; G01R 33/56509; G01R 33/56308; G01R 33/5635; G01R 33/56366
USPC .................................................. 600/407–430
See application file for complete search history.

(56) References Cited

U.S. PATENT DOCUMENTS

| | | | | |
|---|---|---|---|---|
| 2013/0225978 A1* | 8/2013 | Remmele | .............. | A61M 16/01 600/420 |
| 2015/0137813 A1* | 5/2015 | Chenevert | ........ | G01R 33/56341 324/322 |

OTHER PUBLICATIONS

Barger, et al., Time-Resolved Contrast-Enhanced Imaging With Isotropic Resolution and Broad Coverage Using an Undersampled 3D Projection Trajectory, Magnetic Resonance in Medicine, 2002, 48:297-305.

(Continued)

*Primary Examiner* — Sanjay Cattungal
(74) *Attorney, Agent, or Firm* — Quarles & Brady LLP (57) ABSTRACT

A system and method for reconstructing a series of images of a subject includes acquiring medical image data from the subject with a medical imaging system and reconstructing a series of images of the subject from the acquired medical image data set. The reconstructing includes enforcing general adherence to a non-patient-specific signal model that describes a dependency of image intensity values on at least one variable that is associated with a physical or physiological property by constraining reconstruction of individual images in the series of images using the non-patient-specific model. The reconstructing also includes preserving information in the series of images that deviate from the non-patient-specific model by controlling a requirement of consistency with the non-patient-specific model.

17 Claims, 5 Drawing Sheets

(56) References Cited

OTHER PUBLICATIONS

Davenport, The Derivation of the Gamma-Variate Relationship for Tracer Dilution Curves, Journal of Nuclear Medicine, 1983, 24(10):945-948.
Griswold, et al., Partially Parallel Imaging With Localized Sensitivities (PILS), Magnetic Resonance in Medicine, 2000, 44:602-609.
Jeong, et al. Accelerating Time-Resolved MRA With Multiecho Acquisition, Magnetic Resonance in Medicine, 2010, 63:1520-1528.
Jung, et al., k-t FOCUSS: A General Compressed Sensing Framework for High Resolution Dynamic MRI, Magnetic Resonance in Medicine, 2009, 61:103-116.
Korosec, et al., Time-Resolved Contrast-Enhanced 3D MR Angiography, Magnetic Resonance in Medicine, 1996, 36:345-351.
Pruessmann, et al., Advances in Sensitivity Encoding With Arbitrary k-Space Trajectories, Magnetic Resonance in Medicine, 2001, 46:638-651.
Samsonov, et al., Accelerated Serial MR Imaging in Multiple Sclerosis Using Baseline Scan Information, Proc. Intl. Soc. Mag. Reson. Med., 2010, 18:4876.
Van Vaals, et al., "Keyhole" Method for Accelerating Imaging of Contrast Agent Uptake, Journal of Magnetic Resonance Imaging, 1993, 3:671-675.
Velikina, et al., Application of Temporally Constrained Compressed Sensing for High Spatial and Temporal Resolution Intracranial CE MRA, Proc. Intl. Soc. Mag. Reson. Med., 2011, 19:365.
Velikina, et al., An Application of Regularization by Model Consistency Condition to Accelerated Contrast-Enhanced Angiography, Proc. Intl. Soc. Mag. Reson. Med., 2012, 20:13.

\* cited by examiner

SYSTEM AND METHOD FOR ACCELERATED, TIME-RESOLVED IMAGING

STATEMENT REGARDING FEDERALLY SPONSORED RESEARCH

This invention was made with government support under NS065034 awarded by the National Institutes of Health. The government has certain rights in the invention.

BACKGROUND

The present disclosure relates to systems and methods for medical imaging, such as magnetic resonance imaging and computed tomography. More particularly, the invention relates to systems and methods for reconstructing a medical image or a series of medical images.

Increasingly, clinical medicine employs medical imaging to drive clinical decisions and, in some instances, to direct therapeutic or surgical procedures. The non-invasive nature of medical imaging systems, such as magnetic resonance imaging (MRI), computed tomography (CT) imaging, and others, make these systems valuable sources of information about the patient and pathology and even physiology.

Regardless of the imaging system or the clinical purpose, the competing constraints of temporal and spatial resolution (and radiation dose in case of CT imaging) must be balanced with these systems. For example, MRI often has to contend with inherent acquisition speed limits to depict time-varying processes at the desired spatial resolution and coverage. Hence, incomplete sampling strategies followed by application of specialized image reconstruction algorithms have long been a popular strategy to increase effectual MRI speed. In dynamic MRI, such dedicated image reconstruction approaches often rely on various kinds of prior information in spatial and/or temporal dimensions to enhance reconstruction fidelity in these domains.

For example, the clinical need for high spatial and temporal resolution in time-resolved magnetic resonance applications often necessitates image reconstruction from incomplete datasets because the total scan time is limited. This is particularly the case when studying a physiological process because high temporal resolution is often required to acquire the desired information about the physiological process. One such strategy is referred to generally as "parallel imaging." Parallel imaging techniques use spatial information from arrays of radio frequency (RF) receiver coils to compliment the encoding which would otherwise have to be obtained in a sequential fashion using RF pulses and field gradients (such as phase and frequency encoding). Each of the spatially independent receiver coils of the array carries certain spatial information in the form of a sensitivity profile. This information is utilized in order to achieve a complete location encoding by combining the simultaneously acquired coil data from the separate receiver coils. Specifically, parallel imaging techniques can reconstruct undersampled k-space, whereby the number of phase-encoded lines acquired is reduced by increasing the distance between these lines while keeping the maximal extent covered in k-space fixed. The combination of the separate NMR signals produced by the separate receiver coils enables a reduction of the acquisition time required for an image (in comparison to conventional k-space data acquisition) by a factor that, in the most favorable case, equals the number of the receiver coils. Thus, the use of multiple receiver coils acts to increase imaging speed by accelerating the encoding, without increasing gradient switching rates or RF power.

The advent of compressed sensing (CS) provided a new sub-Nyquist sampling requirement for images accepting a sparse representation in some basis. However, the limited spatial sparsity of magnetic resonance images affords only moderate acceleration factors before CS-based reconstructions introduce image blurring and blocky artifacts or other image errors.

Another group of reconstruction approaches employs a data-driven approach, in which low-resolution estimates of the dynamic image series are used to learn a low-rank temporal basis that can be used to represent all temporal behaviors in the time series either exactly or approximately. However, several problems exist in cases with complex temporal behavior of the underlying image series when high accelerations are needed. First, temporal behaviors present in the image series cannot be well represented by a small number of basis functions, while using a large number of basis functions at high accelerations does not improve conditioning of the reconstruction problem and results in amplified noise and/or unresolved aliasing artifacts. Second, there often is a large error stemming from learning the temporal basis from low-resolution images at high accelerations, which propagates into the reconstructed images. Third, higher spatial frequency information cannot be fully restored at high accelerations leading to loss of spatial resolution in the reconstructed images.

Therefore, it would be desirable to have a system and method for further addressing the challenge presented by the competing constraints of temporal resolution or radiation dose versus spatial resolution in medical imaging.

SUMMARY

The disclosure invention overcomes the aforementioned drawbacks by providing a system and method for reconstructing a medical image in which the image reconstruction process is constrained to be consistent with a signal model. In particular, a system and method is provided that utilizes analytical models, not as part of a post-processing technique, but within the reconstruction from highly undersampled data to yield clinically-usable images that accommodate the underlying pathology of the patient, despite the use of the model. The reconstruction of the image is performed with the assumption that temporal progression of each pixel can be described by an analytical function determined by theoretical considerations in each application; however, the reconstruction process is designed to accommodate deviations from the model that reflect underlying pathology or pathologies of the patient.

In accordance with one aspect of the disclosure, a magnetic resonance imaging (MRI) system is disclosed that includes a magnet system configured to generate a polarizing magnetic field about at least a portion of a subject arranged in the MRI system and a magnetic gradient system including a plurality of magnetic gradient coils configured to apply at least one magnetic gradient field to the polarizing magnetic field. The MRI system also includes a radio frequency (RF) system configured to apply an RF field to the subject and to receive magnetic resonance signals from the subject using a coil array and a computer system. The computer system is programmed to control the RF system and the magnetic gradient system to acquire medical image data from the subject in parallel using the coil array and reconstruct a series of images of the subject from the acquired medical image data set. The computer is configured to reconstruct by enforcing general adherence to a non-patient-specific signal model that describes a dependency of image intensity values to at least one variable that is associated with a physical or physiological property by constraining reconstruction of individual images in the series of images using the non-patient-specific model. The computer is also configured reconstruct by preserving information in the series of images that deviate from the non-patient-specific model by controlling a requirement of consistency with the non-patient-specific model.

In accordance with another aspect of the disclosure, a method for reconstructing a series of images of a subject with a medical imaging system is disclosed. The method includes acquiring medical image data from the subject with a medical imaging system and reconstructing a series of images of the subject from the acquired medical image data set. The reconstruction is performed by enforcing general adherence to a non-patient-specific signal model that describes a dependency of image intensity values on at least one variable that is associated with a physical or physiological property by constraining reconstruction of individual images in the series of images using the non-patient-specific model. The reconstruction is also performed by preserving information in the series of images that deviates from the non-patient-specific model by controlling a requirement of consistency with the non-patient-specific model.

In accordance with another aspect of the disclosure, a method for reconstructing a series of images of a subject is disclosed. The method includes acquiring medical image data from the subject with a medical imaging system. The method also includes reconstructing a series of images of the subject from the acquired medical image data set while constraining individual images in the series of images to be consistent with a signal model that describes a dependency of image intensity values on at least one variable that is associated with a physical property of the subject and to be consistent with a motion correction operator.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

In dynamic imaging applications, temporal behavior of the signal is often well approximated by mathematical functions or their combinations. For example, in time-resolved intracranial contrast enhanced MR angiography (CE MRA), the signal in the vessels can be described by a sum of gamma-variate functions. This behavior reflects the physics of contrast propagation through the human cardiovascular system. The same applies to dynamic susceptibility contrast perfusion-weighted imaging (DSC PWI). In many such applications, these modeling functions are used during a post-processing stage to derive quantitative metrics. For example, in DSC PWI, the signal is assumed to follow these functions and is used in the analysis of images to determine arterial input function, calculate cerebral blood volume and flow, and determine mean transit time. These parameters are usually derived after standard image series reconstruction stage by fitting the theoretical model functions to the reconstructed image series.

However, as will be described, the present disclosure provides a system and method that uses a non-patient-specific model, such as a physical or physiological model, to be used during a reconstruction process to provide image quality with less noise and undersampling artifacts than could otherwise be achieved, for example, using acceleration techniques, such as parallel imaging. When combined with parallel imaging, the system and method efficiently reduces noise levels, which is the main limiting factor of parallel imaging, thereby providing higher acceleration capabilities and image quality. Compared to standard view-sharing techniques used in dynamic contrast-enhanced imaging to improve image quality, the systems and methods of the present disclosure preserve temporal fidelity of the reconstructed time series. In applications such as contrast-enhanced, magnetic resonance angiography (CE MRA), this allows for accurate separation of arterial and venous phases of contrast dynamics and estimation of blood volume/blood flow/mean transit times in perfusion imaging. Compared to other techniques based on compressed sensing estimation theory, the systems and methods of the present disclosure improve image sharpness/spatial resolution/temporal resolution. The systems and methods of the present disclosure are also more robust in practice, especially when imaging a disease or pathology where CS assumptions often fail, or in the presence of motion.

Thus, a system and method are provided for reconstructing medical images by employing a model-based reconstruction (MBR) process that utilizes a non-patient-specific model, such as a physical or physiological model. By way of example, a series of medical images can be reconstructed from undersampled medical image data using the provided system and method, particularly where the medical imaging process includes acquiring medical image data that depends on one or more parameters that are known from an analytical or physical model that is not patient specific. As a specific example, this MBR-based image reconstruction is readily applicable to quantitative MRI and various other imaging applications, including CT angiography, requiring time-resolved or spectrally-resolved medical imaging. MBR-based reconstruction can provide significant benefits over existing image reconstruction techniques.

Figure 1:
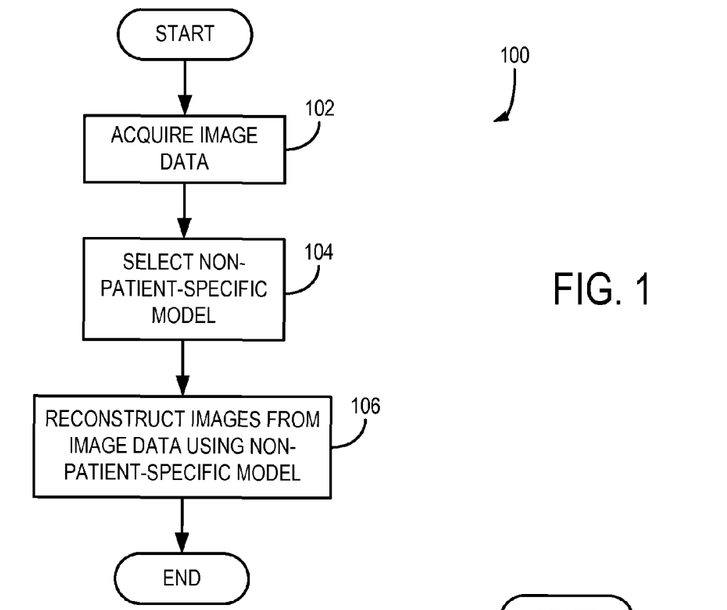
FIG. 1 is a flowchart setting forth the steps of an example of a method for medical image reconstruction using a non-patient-specific model in accordance with the present disclosure.

Turning to FIG. 1, a flow chart 100 is provided for a process using a MBR process that utilizes a non-patient-specific model, such as a physical or physiological model. At process block 102 medical imaging data is acquired. As will be described, the acquisition may be undersampled/accelerated. At process block 104, a general, non-patient-specific model may be selected to provide a priori information to the reconstruction of the image data acquired at process block 10. As will be further described, the non-patient-specific model may be, as a non-limiting example, a model for contrast bolus propagation dynamics. That is, the non-patient-specific model is one that is general to the physical and/or physiological phenomenon being investigated during the imaging study and, thus, need not be created specifically for the patient or subject being imaged. At process block 106, the selected non-patient-specific model is used to as a priori knowledge about the patient, despite not being specific to the patient, to constrain the reconstruction of the acquired image data.

It seems counterintuitive to use a non-patient-specific model within a medical imaging reconstruction process, which by definition and the purpose of a clinical medical application, necessitates patient-specific information, particularly, about underlying pathologies associated with or being sought to be investigated by the imaging study. That is, it would seem that using a non-patient-specific model in a reconstruction process could cause the images to be inaccurate by minimizing the pathological conditions or any structures that deviate from the "standard" that is reflected in the non-patient-specific model. Put another way, using a non-patient-specific model in an image reconstruction process would, to many, seem to risk introducing inaccuracies in the reconstructed images caused by forcing the images to comport with the non-patient-specific model, when the patient may deviate from the non-patient-specific model. However, as will be described, the present disclosure provides a construct that facilitates deviation from the non-patient-specific model during the reconstruction process to overcome this point, while also controlling against pursuing spurious deviations. Furthermore, variations on the technique will be described to improve performance in the presence of patient motion. In this approach, the motion can be estimated either from low-resolution navigators or in an iterative update procedure to correct the image series for application of the model-consistency constraints.

The above-described process can be implanted using any of a variety of imaging modalities, including MRI and CT imaging systems. To explain the details of the general process described with respect to FIG. 1, the following discussion is provided, which utilizes a non-limiting example of an MRI system and makes reference to k-space data. However, other imaging modalities may likewise be used, such as CT systems and the like, with associated data.

In the absence of relaxation effects, the MR signal collected by the $\gamma^{th}$ RF receiver coil out of the total number $n_c$ of coils, with sensitivity $C_\gamma(r)$, from an object, f(r) over a volume-of-interest ("VOI") may be modeled as:

$$s_\gamma(r) = \int_{VOI} e^{ik \cdot r} C_\gamma(r) f(r) dr; \qquad (1)$$

where r and k are image space and k-space coordinate vectors, respectively. In its matrix form, and adding a term for the presence of noise errors, equation (1) can be written as:

$$s = Ef + n \qquad (2);$$

where f is the solution (image) vector corresponding to an arbitrary time frame in the image series, s is a vector of k-space samples from all RF coil receivers, n is noise error, and E is the encoding matrix with elements corresponding to both Fourier and coil sensitivity encoding terms:

$$E_{(m,\gamma),\rho} = e^{ik_m \cdot r_\rho} C_\gamma(r_\rho) \qquad (3).$$

In equation (3), $r_\rho$ and $k_m$ are the discretized spatial and k-space coordinates, respectively. In single-channel MRI acquisitions, the noise can generally be assumed to be identically independently distributed (i.i.d.) Gaussian noise. For multi-channel MRI acquisitions, noise whitening pre-processing using a separately measured noise covariance matrix may used to reduce noise errors. A signal-to-noise ratio (SNR) optimized estimation of the image vector, f, from the k-space data, s, may be generally accomplished by enforcing data consistency in the least squares fashion:

$$\min_f \|Ef - s\|_2; \qquad (4)$$

where $\| \ldots \|_2$ is the $l_2$-norm. In general, the $l_p$-norm of a vector, x, may be written as:

$$\|x\|_p = \left(\sum_i |x_i|^p\right)^{1/p}. \qquad (5)$$

Accelerated MRI techniques rely on incomplete k-space sampling (undersampling), which results in a poorly-conditioned or, in the case of significant undersampling, rank deficient encoding matrix, E. The poor conditioning of the encoding matrix renders solutions to equation (4) sensitive to errors in the k-space data, and the potential rank deficiency of the encoding matrix means that equation (4) will have non-unique solutions. To stabilize estimation of the image vector, f, the proposed model-based approach can be used for regularization of the underdetermined image series reconstruction problem. To isolate a single solution, prior information about the image series as a whole can be used to constrain the solution and, thus, the reconstruction.

That is, the image vector, f, can be represented as a result of evaluation of an analytical function (model) with a given set of model parameters:

$$f = S(\bar{c}, \bar{p}) \qquad (6);$$

where $\bar{c}$ is a set of operator-controlled, or control, parameters, $\bar{p}$ are free (independent) model parameters, and $S(\ldots)$ is a synthesis operator that, for a given set of control parameters, maps the free parameters into the corresponding image series. Control parameters are parameters of pulse sequence and acquisition, which, depending on the type of application may include but not limited to echo time (TE), repetition time (TR), inversion recovery time (TI), and time moment of acquisition of image f. Free parameters may include but not limited to longitudinal relaxation time, $T_1$; transverse relaxation time, $T_2$; apparent transverse relaxation time, $T_2^*$; magnetization, $M_0$; diffusion coefficients; magnetization transfer parameters; separated water signal contribution and separated fat signal contribution; fat fraction; and parameters describing mathematical functions governing contrast bolus propagation.

Let us define the experiment design as a set of vectors of control parameters, each corresponding to an individual measurement:

$$\bar{c} = \{\bar{c}_k\}_{k=1 \ldots N} \qquad (6).$$

Let $$\bar{f}=[f_1 \ldots f_N]^T \quad (7).$$

be a stacked vector of images which correspond to the acquisition with the experiment design $\bar{c}$.

Further, a vector containing parametric (model parameter) maps indicative of the free parameters participating in a given problem formulation can be defined as:

$$\bar{p}=[p_1 \ldots p_M]^T \quad (8).$$

The parametric maps, $\bar{p}$, can be determined through the following equation:

$$\bar{p}=\tilde{S}_{\bar{c}}(\bar{f}) \quad (9);$$

where $\tilde{S}_{\bar{c}}(\ldots)$ is an analysis operator that maps the image series, $\bar{f}$, to the parametric maps, $\bar{p}$. Similarly, let $S_{\bar{c}}$ be the associated synthesis operator that maps from parametric maps to the image series corresponding to $\bar{c}$:

$$\bar{f}=S_{\bar{c}}(\bar{p}) \quad (10);$$

The pixels accurately described by the analytical model can be described by:

$$S_{\bar{c}}(\tilde{S}_{\bar{c}}(\bar{f}))=\bar{f} \quad (11).$$

As will be described, the present disclosure utilizes analytical or non-patient-specific models for the reconstruction of image data, which may be highly undersampled, to yield images. To do so, the reconstruction is performed under the assumption that temporal progression of each pixel can be exactly or approximately described by the analytical or non-patient-specific function or model, determined by theoretical considerations in each application. Generally, the method can be used in any application in which dependence of signal intensity on time/other free parameter can be described by an analytical function or non-patient-specific model.

Figure 2:
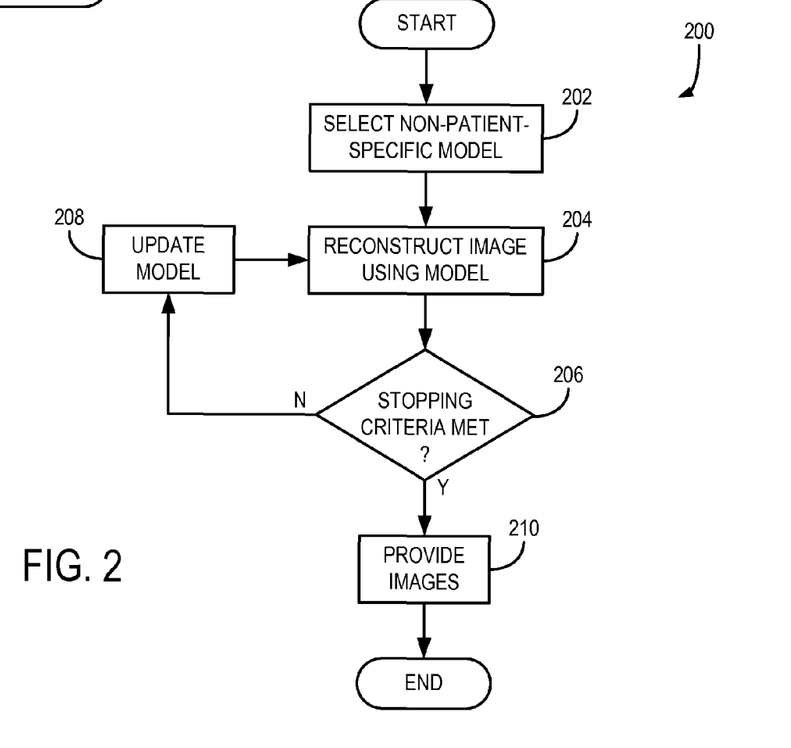
FIG. 2 is a flowchart setting forth the steps of an example of a method for constrained image reconstruction using the non-patient-specific model in accordance with the present disclosure.

Specifically, referring to FIG. 2, steps of a reconstruction process 200 in accordance with the present disclosure begin by seeking to solve the following problem that can be mathematically represented as:

$$\min_{\bar{f}} \|E\bar{f}-\bar{s}\|_2 \text{ subject to } S_{\bar{c}}(\tilde{S}_{\bar{c}}(\bar{f}))=\bar{f}; \quad (12)$$

where $$\bar{E}=\text{diag}(E_1, \ldots, E_N), \bar{s}=[s_1 \ldots s_N]^T \quad (13);$$

are the combined encoding matrix and data vector containing encoding matrices and data vectors for all images in the acquired series, respectively.

The method of the present disclosure can be used to solve equation (12) with the operator D in an iterative reconstruction approach, referred to hereafter as the MBR algorithm. The algorithm alternates between estimation of refined version of the operator D, defined as $D=S_{\bar{c}}\tilde{S}_{\bar{c}}$, using an estimate of the image series on the previous step, and estimation of the next estimate of the image series using the refined version of the operator. A new version of the operator is found on a $k^{th}$ step of the iterative process as a function of image series estimated on the previous $((k-1)^{th})$ step of the iterative process:

$$D_{(k)}=S_{\bar{c}}(\tilde{S}_{\bar{c}}(\bar{f}_{(k-1)})) \quad (14);$$

The sequence of operations required to estimate this operator includes fitting the model to the image series estimate to yield parametric maps of the model, and then use the model to create the synthetic image series, which is used to construct the operator.

In this case, at process block 202, the first (k=1) approximation of the operator $(D_{(1)})$ is determined from the initial (k=0) estimate of the image series $\bar{f}_{(0)}$ and the selected analytical or non-patient-specific model, chosen, for example, as described above, based on the clinical focus of the imaging study being performed. A non-limiting example, in the case of MRI, the non-patient-specific model may relate to time resolved contrast-enhanced magnetic resonance angiography (CE MRA), dynamic susceptibility contrast perfusion-weighted imaging (DSC PWI), or dynamic contrast enhanced perfusion-weighted imaging (DCE-PWI). Additionally, other modalities may benefit from this approach. For example, in contrast-enhanced time-resolved CT angiography the temporal signal may also be described by analytical functions reflecting the physics of contrast propagation throw the human cardio-vascular system.

In turn, the $k^{th}$ approximate of the operator D is used to produce updated version of the image series. This is first accomplished by constructing a sparsifying transform $$\Psi_{(k)}=D_{(k)}D_{(k)}^\dagger-I \quad (15);$$

where I is the identity matrix, and $D^\dagger$ is the pseudoinverse of the operator D, and then solving for $$\bar{f}_{(k)} = \arg\min_{\bar{f}}\{\|E\bar{f}-\bar{s}\|_2 + \lambda\|\Psi_{(k)}\bar{f}\|_p\}. \quad (16)$$

The optimization problem contains two terms: data-fidelity term and non-patient-specific, model-based term. If the second term is pushed close to zero (by biasing the image towards the model), the first term becomes large due to inconsistencies between the acquired data and the solution, the former describing the subject being imaged and the latter of which is describing the model. Therefore, minimal solution should reach a balance between these two quantities.

As described above, this balance is controlled by the $l_p$ norms. The use of $l_1$ or $l_0$ norm to measure the size of the non-patient-specific, model-based term can be used to control undesired weighting toward the model that could otherwise obscure clinically-desired information. Traditional formulation of the compressed-sensing optimization for image reconstruction uses the $l_0$ norm, which simply counts the number of points, for which this term is non-zero, so this is a true measure of sparsity. In the present disclosure, the $l_0$ norm can be replaced with $l_1$ norm, which also produces a sparse solution and does not penalize outliers data, as compared to the non-patient-specific model. Use of the quadratic $l_2$ norm, which squares the size of the deviations, also makes $l_2$ norm value much larger than $l_1$ norm value, so the non-patient-specific, model-based term has more impact on the solution that the data-fidelity term. Thus, in some settings, the $l_1$ norm may be preferred over $l_0$ norm because it is more computationally efficient. However, other norms besides the $l_1$ norm may also be suitable. For example, in some situations, some might consider $l_p$ norms, with $p<=1$. The use of $l_p$ ($p<=1$) norms allows the iterative process to relax the requirement of consistency with the non-patient-specific model if it finds that the fit with the non-patient-specific model is undesirable for a given pixel and precludes simultaneous minimization of the data fidelity term. In still other settings, such as when the non-patient-specific model is believed to fit well with the acquired data, an $l_2$ norm may be used.

The size of the non-patient-specific, model-based term is also regulated by the regularization parameter, $\lambda$, whose quantity affects the balance between the two terms. Choosing a large lambda biases the solution to the non-patient-specific model. Generally, $\lambda$ can be chosen empirically or from theoretical considerations, for example, such as an L-curve method or noise level in the data.

The algorithm alternates between solving equation (14) and equation (16) multiple times starting from the initial estimate $\bar{f}_{(0)}$. Notably, the initial estimate can be estimated by a variety of reconstruction methods, including but not limited to parallel imaging reconstruction, a CS-based reconstruction, a model consistency condition (MOCCO) constrained image reconstruction, a highly constrained projection reconstruction (HYPR), and other reconstruction frameworks.

On each iteration step, image series reconstructed using the operator D at process block 204 is compared at decision block 206 relative to stopping criteria, such that, when outside the tolerance, the operator is updated at process block 208 until the stopping criteria met, at which point a final image series is provided at process block 210.

Standard CS approaches exploit sparsity of the image series after application of general transforms, such as wavelets or spatial/temporal gradients. The above-described technique presents an application-specific approach to transform design. As a non-limiting example, the non-patient-specific model can be one to account for physical properties of contrast dynamics, for example, as used in a CE MRA imaging process. The transform design can be tailored to CE MRA by exploiting the fact that first-pass contrast bolus propagation and recirculation can be modeled. One non-limiting example of a non-patient-specific model of contrast bolus propagation and recirculation may include a linear combination of multiple gamma-variate curves, such as described, for example, in Davenport R, NUCL Med 1984; 24:9454, which is incorporated herein by reference in its entirety. Historically, such curves have been used for post-reconstruction image post-processing. However, as described, the present disclosure provides a construct within which to utilize such non-patient-specific, analytical models to reconstruct images at greater spatial and/or temporal resolutions than could traditionally be achieved.

Figure 3:
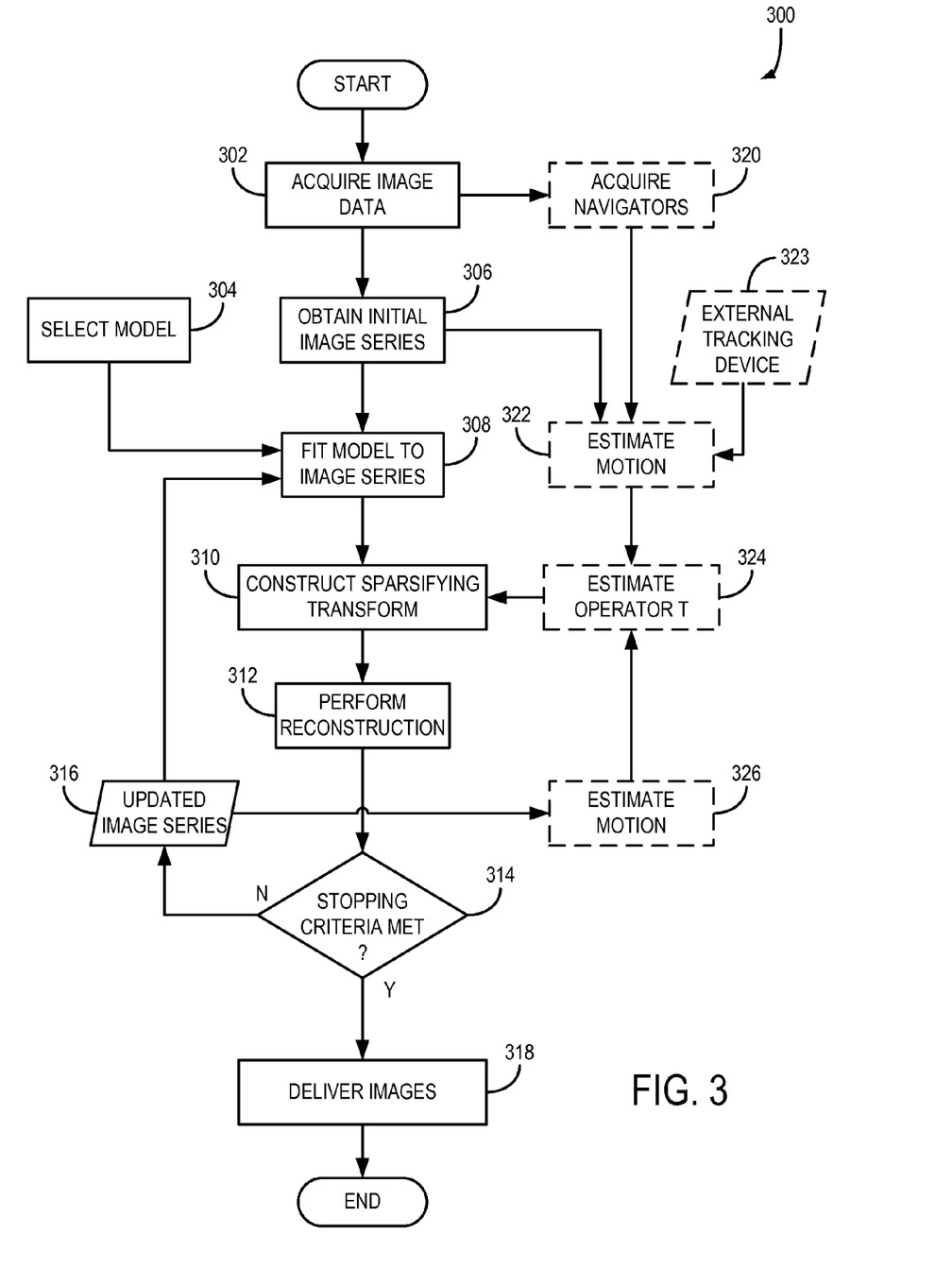
FIG. 3 is a flowchart setting forth the steps of an example of a method for constrained image reconstruction using the non-patient-specific model in accordance with the present disclosure and including an optional motion correction in accordance with the present disclosure.

To continue with this example of a CE MRA imaging process 300 in accordance with the present disclosure, and referring now to FIG. 3, the imaging process may include a parallel imaging process. In this case, data acquisition may be performed at process block 302 using multiple coils. As such, as will be described, the image reconstruction process may be a SENSE reconstruction process, which is known by itself to produce images that may suffer from excessive noise, undersampling artifacts and/or resolution loss (depending on the acquisition type) at high accelerations. A model is selected at process block 304 and, as will be described, is used to reconstruct images. As one non-limiting example, the model may be a non-patient-specific model of contrast propagation. As indicated at process block 306, the acquired image data is used to obtain an initial image series, which is then used at process block 308 to fit the model selected at process block 304 thereto. At process block 310 and in accordance with CS reconstruction processes, a sparsifying transform may be constructed as in equation (15). At process block 312, the CS formulation with model-based penalty term enforces general adherence to the model during the iterative reconstruction, while the use of robust $l_1$ norm preserves temporal dynamics that deviate from the model, for example, such as due to contrast extravasation effects in the case of a non-patient-specific model of contrast dynamics. A stopping criteria is checked at decision block 314. If the stopping criterion is not met, the updated image series created at process block 312 is provided at resource block 316 as the process cycles back to process block 308 where the model is fit to the new image series and at process block 301 to construct a sparsifying transform, at process block 310. Subsequently, at process block 312, the reconstruction is repeated to create an improved time series until final images that meet the stopping criteria are delivered at process block 318. In this example, the number of iterations, for example, of equations (14) and (16), depends on the acceleration factor and potential deviations of the underlying image series from the non-patient-specific, analytical model.

In addition to potential deviations of the underlying image series from the non-patient-specific, analytical model due to pathologies of the patient, inconsistencies may be a result of patient motion. That is, in some cases, the inconsistencies between the underlying image series and analytical model may be caused by motion of the subject during data acquisition. In this case, equation (16) can be modified by the use of a motion correction (MC) operator T describing rigid or non-rigid body motion between time frames, as follows:

$$\bar{f}_{(k)} = \underset{\bar{f}}{\operatorname{argmin}}\{\|E\bar{f} - \bar{s}\|_2 + \lambda\|\Psi_{(k)}T\bar{f}\|_p\}. \quad (17)$$

The application of the operator T aligns individual frames of the image series before invoking the model-based constraint. This operator can be pre-estimated, for example, by acquiring motion estimates from external motion tracking devices or acquisition of navigating k-space data prior to or extracted from the data acquisition at process block 302, as illustrated in optional step 320 of FIG. 3. The data acquired at process block 302 and 320 can be used to estimate patient motion at process block 322 and then the operator T at process block 324. Alternatively, the initial images created at process block 306 may be used or an external tracking device 323 may be used to provide motion tracking data. The operator T can be pre-estimated by an initial image series $\bar{f}^{(0)}$ or by images reconstructed from the navigating data by co-registering each time frame of the image series with the first or another (unperturbed) one, such as at process block 322. Then, during reconstruction, equation (18) may be solved with the same T each time because T is assumed to be known from pre-estimation.

In an alternative implementation, instead of acquiring navigator data at process block 320, operator T can be learned adaptively during reconstruction at process block 326. This adaptive correction uses multiple estimations of the motion operator after each solution of equation (17) followed each time by an update of the operator T with $T_{(k)}$ determined now from the image series $\bar{f}^{(k)}$. Thus, this construct can be readily integrated with the MBR process described above with respect to FIGS. 1-3, as illustrated in FIG. 3. That is, in this case, the reconstruction is performed at process block 312 with motion correction in place and the stopping criteria at decision block 314 has two considerations: (1) analysis of the model, as described above, and (2) analysis of the motion parameters created at process block 326 versus the motion parameters estimated at the previous step. These considerations may be analyzed using a variety of processes. As one non-limiting example, a user may select a predetermined number of passes that is predetermined to satisfy the stopping criteria. As another non-limiting example, the stopping criteria can be based on a deviation metric evaluated through a comparison of the results of a most-recent pass versus a prior pass. If the deviation found in the comparison is smaller than a predetermined metric, the stopping criteria is satisfied. Notably, the two considerations may both be evaluated in this manner. That is, updates of model update and updates of motion transform may both be evaluated at decision block 314. The criterion for the former may be the changes in images reconstructed on two consequent passes iterations, and the criterion of the latter may be the changes in motion parameters obtained on the same passes.

Figure 4:
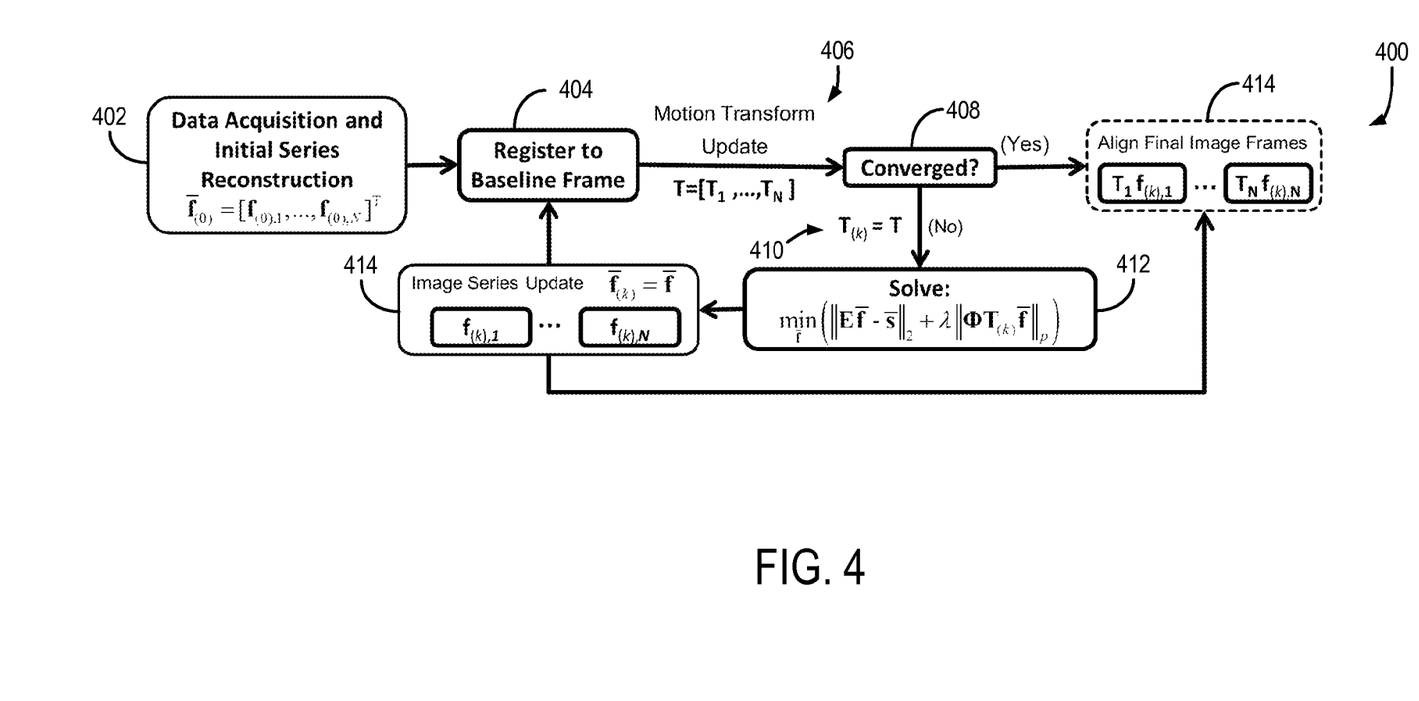
FIG. 4 is a flowchart setting forth the steps of an example of a method for motion correction in accordance with the present disclosure.

However, the above-described motion correction process can also be utilized separately for any compressed sensing (CS) process. For example, when performing a CS-based image reconstruction, the use of $l_1$ norm in it can be used to make reconstruction less sensitive to sharp signal changes, in particular, caused by motion. However, the above-mentioned adaptive process makes such a CS-based reconstruction further robust to motion. Referring to FIG. 4, a process is illustrated that alternates between co-registration of image estimates to obtain rigid body transformations (T) and the reconstruction step given by:

$$\overline{f}_{(k)} = \underset{\overline{f}}{\operatorname{argmin}} \{\|E\overline{f} - \overline{s}\|_2 + \lambda \|\Phi T_{(k)} \overline{f}\|_p\} \quad (18)$$

where transformations T are combined with the arbitrary CS transform ($\Phi$) designed for a particular application to align the images in $\overline{f}$ before invoking a CS constraint, resulting in a motion-adaptive transform. Such a motion correction process 400 begins with the acquisition of a time series of data and reconstruction at process block 402, which is used to create a baseline at process block 404. For example, in a spiral acquisition, as each spiral shot is assigned to a separate time frame, the first (data fidelity) term is applied to unperturbed time frames to maintain consistency with the acquired data. Other possible acquisition schemes may include but not limited to radial acquisition, where the subset of acquired projections is assigned to a separate time frame. This allows a transformation T to be created at 406 in a manner similar to that described above with respect to FIG. 3, whereby, convergence is checked at block 408 and transformation T is updated at 410 if no convergence is found. Thereafter, at process block 412, equation (18) is solved and the image series is updated at process block 414, and the process iterates. After convergence is found at block 408, final transformations T are applied at process block 414 to align images for final display or quantitative analysis. The above-described motion-adaptive CS technique can be used to significantly improve image-derived quantitative metrics, such as cerebral blood flow/volume maps in perfusion MRI.

The above-described model-based reconstruction (MBR) techniques and motion corrections, alone or in combination, may be used with a wide variety of imaging modalities and clinical applications. As described above, the techniques may be utilized with CS-based reconstruction, MOCCO constrained image reconstruction, HYPR, and other reconstruction frameworks. With respect to MOCCO constrained image reconstruction the reconstruction of image series for parameter mapping, such as T1/T2 mapping, and also analytical models of signal evolution, can benefit from the above-described MBR and motion correction, including both the above-described navigator-based and the adaptive motion corrections.

Figure 5:
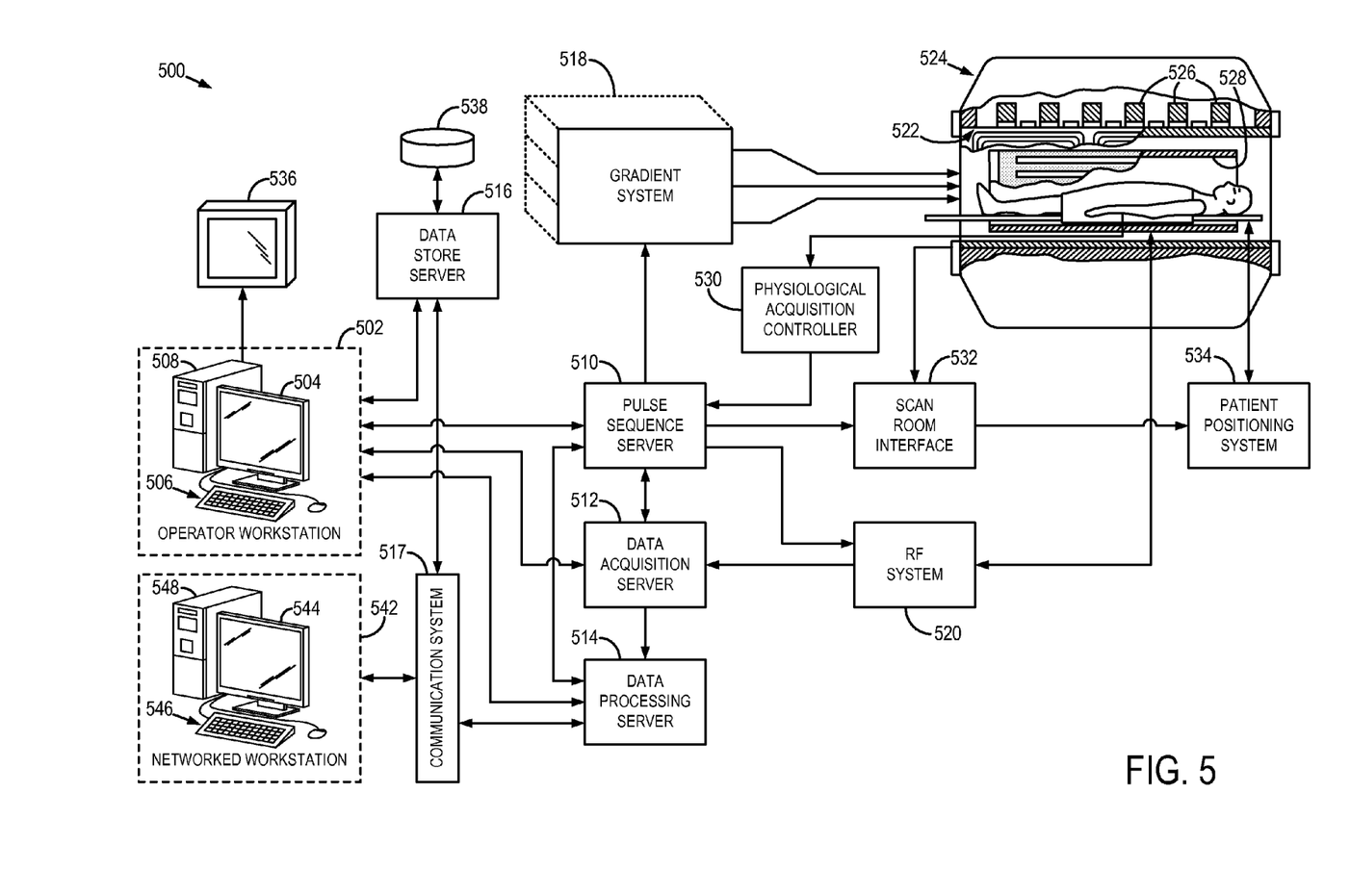
FIG. 5 is a block diagram of an example of a magnetic resonance imaging system, which may be configured to perform in accordance with the present disclosure.

By way of example, the aforementioned image reconstruction and motion correction methods may be implemented in MRI, CT, and other imaging applications. Referring particularly now to FIG. 5, an example of an MRI system 100 is illustrated. Thereafter, with reference to FIG. 6, a CT system such as may be used with the present disclosure will be described.

The MRI system 500 includes an operator workstation 502, which will typically include a display 504, one or more input devices 506, such as a keyboard and mouse, and a processor 508. The processor 508 may include a commercially available programmable machine running a commercially available operating system. The operator workstation 502 provides the operator interface that enables scan prescriptions to be entered into the MRI system 500. In general, the operator workstation 502 may be coupled to four servers: a pulse sequence server 510; a data acquisition server 512; a data processing server 514; and a data store server 516. The operator workstation 502 and each server 510, 512, 514, and 516 are connected to communicate with each other. For example, the servers 510, 512, 514, and 516 may be connected via a communication system 517, which may include any suitable network connection, whether wired, wireless, or a combination of both. As an example, the communication system 517 may include both proprietary or dedicated networks, as well as open networks, such as the internet.

The pulse sequence server 510 functions in response to instructions downloaded from the operator workstation 502 to operate a gradient system 518 and a radiofrequency (RF) system 520. Gradient waveforms necessary to perform the prescribed scan are produced and applied to the gradient system 518, which excites gradient coils in an assembly 522 to produce the magnetic field gradients and used for position encoding magnetic resonance signals. The gradient coil assembly 522 forms part of a magnet assembly 524 that includes a polarizing magnet 126 and a whole-body RF coil 528.

RF waveforms are applied by the RF system 520 to the RF coil 128, or a separate local coil (not shown in FIG. 5), in order to perform the prescribed magnetic resonance pulse sequence. Responsive magnetic resonance signals detected by the RF coil 528, or a separate local coil, are received by the RF system 520, where they are amplified, demodulated, filtered, and digitized under direction of commands produced by the pulse sequence server 510. The RF system 520 includes an RF transmitter for producing a wide variety of RF pulses used in MRI pulse sequences. The RF transmitter is responsive to the scan prescription and direction from the pulse sequence server 510 to produce RF pulses of the desired frequency, phase, and pulse amplitude waveform. The generated RF pulses may be applied to the whole-body RF coil 528 or to one or more local coils or coil arrays.

The RF system 520 also includes one or more RF receiver channels. Each RF receiver channel includes an RF preamplifier that amplifies the magnetic resonance signal received by the coil 528 to which it is connected, and a detector that detects and digitizes the quadrature components of the received magnetic resonance signal. The magnitude of the received magnetic resonance signal may, therefore, be determined at any sampled point by the square root of the sum of the squares of the and components:

$$M = \sqrt{I^2 + Q^2} \quad (15);$$

and the phase of the received magnetic resonance signal may also be determined according to the following relationship:

$$\varphi = \tan^{-1}\left(\frac{Q}{I}\right). \quad (16)$$

The pulse sequence server 510 also optionally receives patient data from a physiological acquisition controller 530. By way of example, the physiological acquisition controller 530 may receive signals from a number of different sensors connected to the patient, such as electrocardiograph (ECG) signals from electrodes, or respiratory signals from respiratory bellows or other respiratory monitoring device. Such signals are typically used by the pulse sequence server 510 to synchronize, or "gate," the performance of the scan with the subject's heart beat or respiration.

The pulse sequence server 510 also connects to a scan room interface circuit 532 that receives signals from various sensors associated with the condition of the patient and the magnet system. It is also through the scan room interface circuit 532 that a patient positioning system 534 receives commands to move the patient to desired positions during the scan.

The digitized magnetic resonance signal samples produced by the RF system 520 are received by the data acquisition server 512. The data acquisition server 512 operates in response to instructions downloaded from the operator workstation 502 to receive the real-time magnetic resonance data and provide buffer storage, such that no data is lost by data overrun. In some scans, the data acquisition server 512 does little more than passing the acquired magnetic resonance data to the data processor server 514. However, in scans that require information derived from acquired magnetic resonance data to control the further performance of the scan, the data acquisition server 512 is programmed to produce such information and convey it to the pulse sequence server 510. For example, during prescans, magnetic resonance data is acquired and used to calibrate the pulse sequence performed by the pulse sequence server 510. As another example, navigator signals may be acquired and used to adjust the operating parameters of the RF system 520 or the gradient system 518, or to control the view order in which k-space is sampled. In still another example, the data acquisition server 512 may also be employed to process magnetic resonance signals used to detect the arrival of a contrast agent in a magnetic resonance angiography (MRA) scan. By way of example, the data acquisition server 512 acquires magnetic resonance data and processes it in real-time to produce information that is used to control the scan.

The data processing server 514 receives magnetic resonance data from the data acquisition server 512 and processes it in accordance with instructions downloaded from the operator workstation 502. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 514 are conveyed back to the operator workstation 502 where they are stored. Real-time images are stored in a data base memory cache (not shown in FIG. 5), from which they may be output to operator display 512 or a display 536 that is located near the magnet assembly 524 for use by attending physicians. Batch mode images or selected real time images are stored in a host database on disc storage 538. When such images have been reconstructed and transferred to storage, the data processing server 514 notifies the data store server 516 on the operator workstation 502. The operator workstation 502 may be used by an operator to archive the images, produce films, or send the images via a network to other facilities.

The MRI system 500 may also include one or more networked workstations 542. By way of example, a networked workstation 542 may include a display 544; one or more input devices 546, such as a keyboard and mouse; and a processor 548. The networked workstation 542 may be located within the same facility as the operator workstation 502, or in a different facility, such as a different healthcare institution or clinic.

The networked workstation 542, whether within the same facility or in a different facility as the operator workstation 502, may gain remote access to the data processing server 514 or data store server 516 via the communication system 517. Accordingly, multiple networked workstations 542 may have access to the data processing server 514 and the data store server 516. In this manner, magnetic resonance data, reconstructed images, or other data may be exchanged between the data processing server 514 or the data store server 516 and the networked workstations 542, such that the data or images may be remotely processed by a networked workstation 542. This data may be exchanged in any suitable format, such as in accordance with the transmission control protocol (TCP), the internet protocol (IP), or other known or suitable protocols.

The above-described proposed MBR approach was tested in simulations and aneurysm patient studies conducted using an MRI system 500, such as described above. In particular, the system was a 3.0 Tesla clinical scanner with an 8-channel head coil using a hybrid radial (in-plane)/Cartesian (through-plane) acquisition during a contrast injection. The scan parameters were TE/TR=1.5/4 ms, FA=25°, BW=125 kHz, 20 slices, voxel size 0.86×0.86×2 mm3. The data were reconstructed from 15 projections/slice per 1.2 s time frame (acceleration factor R=27) using iterative SENSE, standard CS, and the proposed MBR. Arterial phase frame (AF) was reconstructed by PILS combining projections from 8 frames (R=3.3), which were reconstructed separately by MBR and averaged to get AF.

Images were reconstructed that illustrate improved spatial resolution of MBR reconstruction of the aneurysm patient data for each slice, which translated into better visualization and delineation of small vessels in the MIP images. Spatial resolution gained using MBR over SENSE and standard CS was further confirmed by examining pair-wise image differences, which showed that MBR restores most higher spatial frequency information compared to SENSE and standard CS. MBR restored the arterial frame with resolution comparable to gridding-based PILS approach but with much improved SNR. MBR preserved temporal dynamics of SENSE in large (not-affected by resolution loss) structure (aneurysm) and improved the waveform in the smaller (resolution-affected) structure (aneurysm feeding artery).

Thus, the above-described MBR process, which is a data-driven, model-based CS reconstruction, showed the ability to improve spatial resolution and SNR in highly accelerated CE MRA. Moreover, MBR was able to preserve temporal dynamics of contrast propagation in both normal and pathological vessels. Using the application-specific transform that exploits physical properties of contrast dynamics made the approach more efficient than standard CS methods relying on transforms inherited from general image processing field. The method also improved spatial and temporal fidelity in other application based on first pass bolus tracking such, as dynamic susceptibility perfusion weighted MRI. Furthermore, as mentioned above, the methods can be employed with other imaging modalities, such as a CT imaging system, such as described below, which could benefit from the advantages in clinical applications such as time-resolved CT angiography.

Figure 6:
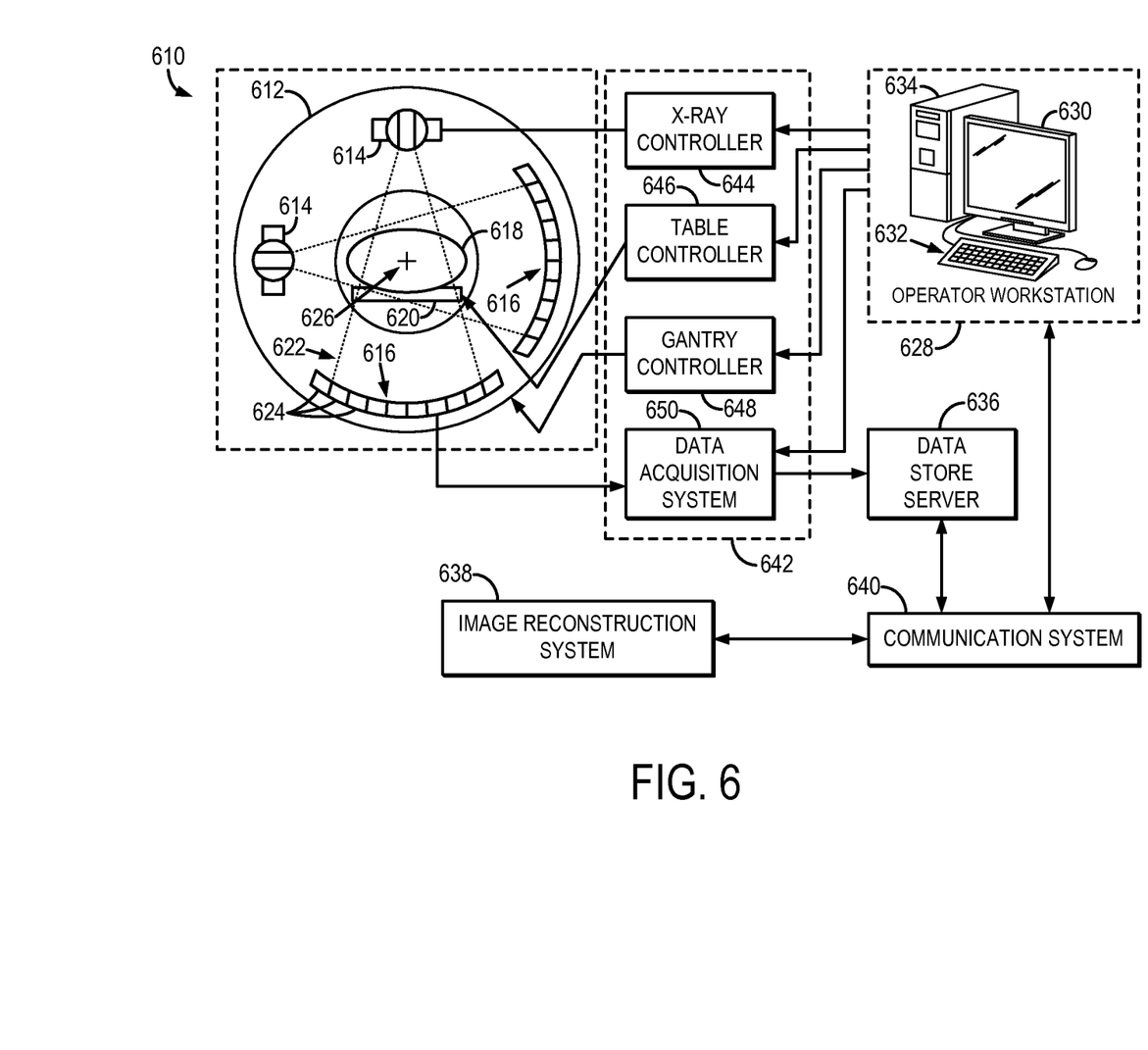
FIG. 6 is a block diagram of an example of a computed tomography system, which may be configured to perform in accordance with the present disclosure

Referring to FIG. 6, a CT system 610 generally include a gantry 612 fitted with a X-ray tube 614 or, in some cases, two X-ray tubes, and an opposing detector assembly 616, which, together, rotate about a subject 618 arranged on a patient bed 620 to acquire multiple projections for reconstructing an image. The x-ray source 614 projects an x-ray beam 622, which may be a fan-beam or cone-beam of x-rays, towards the detector array 616 on the opposite side of the gantry 612. The detector array 616 includes a number of x-ray detector elements 624. Together, the x-ray detector elements 624 sense the projected x-rays 622 that pass through the subject 618, such as a medical patient or an object undergoing examination, who is positioned in the CT system 610. Each x-ray detector element 624 produces an electrical signal that may represent the intensity of an impinging x-ray beam and, hence, the attenuation of the beam as it passes through the subject 618. In some configurations, each x-ray detector 624 is capable of counting the number of x-ray photons that impinge upon the detector 624. During a scan to acquire x-ray projection data, the gantry 612 and the components mounted thereon rotate about a center of rotation 626 located within the CT system 610.

The CT system 610 also includes an operator workstation 628, which typically includes a display 630; one or more input devices 632, such as a keyboard and mouse; and a computer processor 634. The computer processor 634 may include a commercially available programmable machine running a commercially available operating system. The operator workstation 628 provides the operator interface that enables scanning control parameters to be entered into the CT system 610. In general, the operator workstation 628 is in communication with a data store server 636 and an image reconstruction system 638. By way of example, the operator workstation 628, data store sever 636, and image reconstruction system 638 may be connected via a communication system 640, which may include any suitable network connection, whether wired, wireless, or a combination of both. As an example, the communication system 640 may include both proprietary or dedicated networks, as well as open networks, such as the internet.

The operator workstation 628 is also in communication with a control system 642 that controls operation of the CT system 610. The control system 642 generally includes an x-ray controller 644, a table controller 646, a gantry controller 648, and a data acquisition system 650. The x-ray controller 44 provides power and timing signals to the x-ray source 614 and the gantry controller 648 controls the rotational speed and position of the gantry 612. The table controller 646 controls the table 620 to position the subject 618 in the gantry 612 of the CT system 610.

A data acquisition system (DAS) 650 samples data from the detector elements 624 and converts the data to digital signals for subsequent processing. For instance, digitized x-ray data is communicated from the DAS 650 to the data store server 636. The image reconstruction system 38 then retrieves the x-ray data from the data store server 636 and reconstructs an image therefrom. The image reconstruction system 638 may include a commercially available computer processor, or may be a highly-parallel computer architecture, such as a system that includes multiple-core processors and massively parallel, high-density computing devices. Optionally, image reconstruction can also be performed on the processor 634 in the operator workstation 628. Reconstructed images can then be communicated back to the data store server 636 for storage or to the operator workstation 628 to be displayed to the operator or clinician.

The above described systems and methods provide improved spatial resolution and visualization of small features (vessels, lesions, and the like), improved robustness to imaging imperfections and patient motion. Furthermore, the systems and methods provide better image signal-to-noise ratio (SNR) and more flexibility than traditional methods. More particularly, the above-described systems and methods provide image quality with less noise than parallel imaging alone. When combined with parallel imaging, it efficiently reduces noise levels, the main limiting factor of parallel imaging, thereby providing higher acceleration capabilities and image quality. Compared to standard view-sharing techniques used in dynamic contrast-enhanced imaging to improve image quality, the above-described systems and methods preserve temporal fidelity of the reconstructed time series, allowing accurate separation of arterial and venous phases of contrast dynamics (in CE MRA) and estimation of blood volume/blood flow/mean transit times in perfusion imaging. Compared to other techniques based on compressed sensing estimation theory, the above-described systems and methods improve image sharpness/spatial-temporal resolution, which was demonstrated as described above.

In summary, the above-described systems and method can be used with a variety of clinical applications. For example, the above-described systems and methods can be used to perform highly accelerated dynamic contrast-enhanced imaging including MR angiography with improved visualization of small features and high SNR. The technology may be also useful for time resolved CT angiography and perfusion imaging where the proposed technology may lead to the significant dose reduction. Further still, the above-described systems and methods may be used for parameter mapping. In addition, these processes or others may or may not be used for motion corrects, such as described above.

The present invention has been described in terms of one or more preferred embodiments, and it should be appreciated that many equivalents, alternatives, variations, and modifications, aside from those expressly stated, are possible and within the scope of the invention.

As used in the claims, the phrase "at least one of A, B, and C" means at least one of A, at least one of B, and/or at least one of C, or any one of A, B, or C or combination of A, B, or C. A, B, and C are elements of a list, and A, B, and C may be anything contained in the Specification.

The invention claimed is:

1. A magnetic resonance imaging (MRI) system, comprising:
    a magnet system configured to generate a polarizing magnetic field about at least a portion of a subject arranged in the MRI system;
    a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals from the subject using a coil array;

a computer system programmed to:

control the RF system and the magnetic gradient system to acquire medical image data from the subject in parallel using the coil array;

reconstruct a series of images of the subject from the acquired medical image data set by:

enforcing general adherence to a non-patient-specific signal model that describes a dependency of image intensity values on at least one variable that is associated with a physical or physiological property by constraining reconstruction of individual images in the series of images using the non-patient-specific model; and preserving information in the series of images that deviate from the non-patient-specific model by controlling a requirement of consistency with the non-patient-specific model.

2. The system of claim 1 wherein the computer system is further programmed to control the requirement of consistency with the non-patient-specific model by relaxing the requirement of consistency with the non-patient-specific model if a fit with the non-patient-specific model is undesirable for a given pixel in an image in the series of images.

3. A method for reconstructing a series of images of a subject, the steps of the method comprising:

a) acquiring medical image data from the subject with a medical imaging system;

b) reconstructing a series of images of the subject from the acquired medical image data set by:

i) enforcing general adherence to a non-patient-specific signal model that describes a dependency of image intensity values on at least one variable that is associated with a physical or physiological property by constraining reconstruction of individual images in the series of images using the non-patient-specific model; and ii) preserving information in the series of images that deviate from the non-patient-specific model by controlling a requirement of consistency with the non-patient-specific model.

4. The method of claim 3 wherein the non-patient-specific signal model includes a model for contrast bolus propagation dynamics.

5. The method of claim 3 wherein reconstructing the series of images includes performing an iterative reconstruction process.

6. The method of claim 5 wherein controlling the requirement of consistency with the non-patient-specific model is performed by relaxing the requirement of consistency with the non-patient-specific model if a fit with the non-patient-specific model is undesirable for a given pixel in an image in the series of images.

7. The method of claim 5 wherein reconstructing the series of images of the subject includes iteratively minimizing an optimization problem having a data-fidelity term and a non-patient-specific, model-based term.

8. The method of claim 7 wherein controlling the requirement of consistency with the non-patient-specific model includes precluding simultaneous minimization of the data fidelity term with relaxation of the non-patient-specific, model-based term.

9. The method of claim 7 wherein a balance is reached between the data-fidelity term and the non-patient-specific, model-based term using $l_p$ norms, wherein the $l_p$ norm for the data-fidelity term is p=1 and the $l_p$ norm for the data non-patient-specific, model-based term is p<=1.

10. The method of claim 3 wherein the non-patient-specific model relates to time resolved contrast-enhanced magnetic resonance angiography (CE MRA), dynamic susceptibility contrast perfusion-weighted imaging (DSC PWI), or dynamic contrast enhanced perfusion-weighted imaging (DCE-PWI.

11. The method of claim 3 wherein the medical imaging system includes a magnetic resonance imaging system or a computed tomography system.

12. The method of claim 3 wherein the non-patient-specific signal model describes signal evolution in a serial dimension of the series of images.

13. The method of claim 3 further comprising performing a motion correction process by incorporating a motion correction operator into reconstructing the series of images of the subject, that aligns individual images in the series of images before invoking the non-patient-specific, signal model.

14. The method of claim 13 further comprising estimating the motion correction operator by:

acquiring motion tracking data and estimating the motion correction operator from the motion tracking data;

estimating the motion correction operator by co-registering each image in the series of images another image in the series of images; or adaptively estimating the motion correction operator during the reconstruction.

15. The method of claim 14 wherein the motion tracking data is acquired from one of separately-acquired navigator sampling, navigator data derived from the medical image data, or an external tracking device.

16. The method of claim 3 wherein step b) includes using at least one of a compressed sensing-based reconstruction, a model consistency condition (MOCCO) constrained image reconstruction, or a highly constrained projection reconstruction (HYPR) processes.

17. The method of claim 3 wherein step b) includes generating parameter map of the subject.

* * * * *

UNITED STATES PATENT AND TRADEMARK OFFICE
CERTIFICATE OF CORRECTION

PATENT NO. : 9,770,223 B2
APPLICATION NO. : 14/481790
DATED : September 26, 2017
INVENTOR(S) : Alexey A. Samsonov et al.

It is certified that error appears in the above-identified patent and that said Letters Patent is hereby corrected as shown below:

In the Specification

Column 5, Line 11, "10" should be -- 102 --.

Column 6, Line 22, "l$_2$" should be -- $\ell_2$ --.

Column 6, Line 22, "l$_p$" should be -- $\ell_p$ --.

Column 8, Line 43, "l$_p$" should be -- $\ell_p$ --.

Column 8, Line 44, "l$_1$ or l$_0$" should be -- $\ell_1$ or $\ell_0$ --.

Column 8, Line 49, "l$_0$" should be -- $\ell_0$ --.

Column 8, Line 51, "l$_0$" should be -- $\ell_0$ --.

Column 8, Line 52, "l$_1$" should be -- $\ell_1$ --.

Column 8, Line 55, "l$_2$" should be -- $\ell_2$ --.

Column 8, Line 56, "l$_2$" should be -- $\ell_2$ --.

Column 8, Line 56, "l$_1$" should be -- $\ell_1$ --.

Column 8, Line 59, "l$_1$" should be -- $\ell_1$ --.

Column 8, Line 59, "l$_0$" should be -- $\ell_0$ --.

Column 8, Line 61, "l$_1$" should be -- $\ell_1$ --.

Signed and Sealed this
Fourth Day of December, 2018

Andrei Iancu
*Director of the United States Patent and Trademark Office*

CERTIFICATE OF CORRECTION (continued)
U.S. Pat. No. 9,770,223 B2

Column 8, Line 62, "$l_p$" should be -- $\ell_p$ --.

Column 8, Line 63, "$l_p$" should be -- $\ell_p$ --.

Column 9, Line 2, "$l_2$" should be -- $\ell_2$ --.

Column 10, Line 1, "$l_1$" should be -- $\ell_1$ --.

Column 14, Line 42, "FA=25°" should be -- FA=25o --.

In the Claims

Column 18, Claim 9, Line 12, "$l_p$" should be -- $\ell_p$ --.

Column 18, Claim 9, Line 12, "$l_p$" should be -- $\ell_p$ --.

Column 18, Claim 9, Line 13, "$l_p$" should be -- $\ell_p$ --.

Column 18, Claim 10, Line 21, "(DCE-PWI." should be -- (DCE-PWI). --.